United States Patent
Nixon et al.

(10) Patent No.: US 11,020,248 B2
(45) Date of Patent: *Jun. 1, 2021

(54) VACUUM SYSTEM FOR A PROSTHETIC FOOT

(71) Applicant: Ability Dynamics, LLC, Tempe, AZ (US)

(72) Inventors: Kodi Nixon, Mesa, AZ (US); Brian Werner, Mesa, AZ (US); James M. Scott, Phoenix, AZ (US); Gene Parker, Mesa, AZ (US)

(73) Assignee: Proteor USA, LLC, Tempe, AZ (US)

( * ) Notice: Subject to any disclaimer, the term of this patent is extended or adjusted under 35 U.S.C. 154(b) by 126 days.

This patent is subject to a terminal disclaimer.

(21) Appl. No.: 16/289,959

(22) Filed: Mar. 1, 2019

(65) Prior Publication Data
US 2019/0192315 A1    Jun. 27, 2019

Related U.S. Application Data

(63) Continuation-in-part of application No. 16/111,569, filed on Aug. 24, 2018, now Pat. No. 10,842,653, (Continued)

(51) Int. Cl.
*A61F 2/66* (2006.01)
*A61F 2/68* (2006.01)
(Continued)

(52) U.S. Cl.
CPC ............... *A61F 2/66* (2013.01); *A61F 2/68* (2013.01); *A61F 2002/501* (2013.01);
(Continued)

(58) Field of Classification Search
CPC .................................................. A43B 7/082
(Continued)

(56) References Cited

U.S. PATENT DOCUMENTS 3,331,546 A    7/1967   Brunelle
4,578,082 A    3/1986   Sen-Jang
(Continued)

FOREIGN PATENT DOCUMENTS

CA    2054588    5/1999
CN    2089799 U    8/1990
(Continued)

OTHER PUBLICATIONS

Roland D. Christensen, U.S. Appl. No. 09/607,494 for "Prosthetic Foot," filed Jun. 30, 2000, abandoned Oct. 29, 2002.
(Continued)

*Primary Examiner* — Marcia L Watkins
(74) *Attorney, Agent, or Firm* — The Noblitt Group, PLLC

(57) ABSTRACT

A prosthetic foot comprising a vacuum system configured to attach to a vacuum attachment apparatus and a residual limb. The prosthetic foot may comprise a resilient bottom member, a resilient top member, and a vacuum system. The resilient bottom member may comprise a front end and a rear end. The resilient top member may comprise a front end and a rear end and the front end of the resilient top member may be connected to the front end of the resilient bottom member. The vacuum system may be coupled to an underside of the rear end of the top member. The vacuum system may comprise a compressible member, a chamber located within the compressible member, a universal valve system received within the compressible member, a passageway connecting the valve system and the chamber, and an air return coupled to the valve system and the vacuum attachment apparatus.

19 Claims, 16 Drawing Sheets

Related U.S. Application Data which is a continuation-in-part of application No. 14/976,129, filed on Dec. 21, 2015, now abandoned, which is a continuation of application No. 14/731,818, filed on Jun. 5, 2015, now abandoned, which is a continuation of application No. 13/568,535, filed on Aug. 7, 2012, now abandoned, application No. 16/289,959, which is a continuation-in-part of application No. 16/111,569, which is a continuation-in-part of application No. 14/976,129, which is a continuation of application No. 14/731,818, which is a continuation of application No. 13/568,535, which is a continuation-in-part of application No. PCT/US2011/033319, filed on Apr. 20, 2011, which is a continuation-in-part of application No. 12/799,215, filed on Apr. 20, 2010, now abandoned, which is a continuation-in-part of application No. 11/901,845, filed on Sep. 19, 2007, now Pat. No. 8,048,173, application No. 16/289,959, which is a continuation-in-part of application No. 16/111,569, which is a continuation-in-part of application No. 14/731,818, which is a continuation of application No. 13/568,535, which is a continuation-in-part of application No. PCT/US2011/033319, filed on Apr. 20, 2011, which is a continuation-in-part of application No. 12/799,215, which is a continuation-in-part of application No. 11/901,845, application No. 16/289,959, which is a continuation-in-part of application No. 16/111,569, which is a continuation-in-part of application No. 14/731,771, filed on Jun. 5, 2015, now abandoned, which is a continuation of application No. 13/642,501, filed as application No. PCT/US2011/033319 on Apr. 20, 2011, now Pat. No. 9,078,773, which is a continuation-in-part of application No. 12/799,215, filed on Apr. 20, 2010, now abandoned, which is a continuation-in-part of application No. 11/901,845.

(60) Provisional application No. 62/550,107, filed on Aug. 25, 2017, provisional application No. 62/589,025, filed on Nov. 21, 2017.

(51) Int. Cl.
  *A61F 2/80* (2006.01)
  *A61F 2/50* (2006.01)
  *A61F 2/74* (2006.01)

(52) U.S. Cl.
  CPC .............. *A61F 2002/5009* (2013.01); *A61F 2002/6614* (2013.01); *A61F 2002/6642* (2013.01); *A61F 2002/6664* (2013.01); *A61F 2002/6671* (2013.01); *A61F 2002/742* (2013.01); *A61F 2002/748* (2013.01); *A61F 2002/802* (2013.01)

(58) Field of Classification Search
  USPC ........ 623/26–46; 417/480, 478, 472; 36/3 R, 36/3 B
  See application file for complete search history.

(56) References Cited

U.S. PATENT DOCUMENTS

| | | |
|---|---|---|
| 4,822,363 A | 4/1989 | Phillips |
| 5,062,859 A | 11/1991 | Naeder |
| 5,112,356 A | 5/1992 | Harris et al. |
| 5,116,382 A | 5/1992 | Wilson et al. |
| 5,156,632 A | 10/1992 | Wellershaus |
| 5,258,039 A | 11/1993 | Goh et al. |
| 5,352,189 A | 10/1994 | Schumann et al. |
| 5,443,522 A | 8/1995 | Hiemisch |
| 5,443,528 A | 11/1995 | Allen |
| 5,514,186 A | 5/1996 | Phillips |
| 5,653,767 A | 8/1997 | Allen |
| 5,701,686 A | 12/1997 | Herr |
| 5,766,265 A | 6/1998 | Phillips |
| 5,888,239 A | 3/1999 | Wellershaus et al. |
| 5,897,594 A | 4/1999 | Martin et al. |
| 5,944,760 A | 8/1999 | Christensen |
| 5,954,075 A | 9/1999 | Gilmour |
| 5,993,488 A | 11/1999 | Phillips |
| 6,077,301 A | 6/2000 | Pusch |
| 6,099,572 A | 8/2000 | Mosler et al. |
| 6,120,547 A | 9/2000 | Christensen |
| 6,197,068 B1 | 3/2001 | Christensen |
| 6,241,776 B1 | 6/2001 | Christensen |
| 6,261,324 B1 | 7/2001 | Merlette |
| 6,406,500 B1 | 6/2002 | Phillips |
| 6,645,253 B2 | 11/2003 | Caspers |
| 6,663,673 B2 | 12/2003 | Christensen |
| 6,669,737 B2 | 12/2003 | Mosler et al. |
| 6,702,858 B2 | 3/2004 | Christensen |
| 6,712,860 B2 | 3/2004 | Rubie et al. |
| 6,764,522 B1 | 7/2004 | Cehn |
| 6,767,370 B1 | 7/2004 | Mosler et al. |
| 6,805,717 B2 | 10/2004 | Christensen |
| 6,811,571 B1 | 11/2004 | Phillips |
| 6,852,131 B1 | 2/2005 | Chen et al. |
| 6,875,241 B2 | 4/2005 | Christensen |
| 6,875,242 B2 | 4/2005 | Christensen |
| 6,911,052 B2 | 6/2005 | Christensen |
| 6,929,665 B2 | 8/2005 | Christensen |
| 6,942,704 B2 | 9/2005 | Sulprizio |
| 6,966,933 B2 | 11/2005 | Christensen |
| 6,972,043 B1 | 12/2005 | Biedermann et al. |
| 7,063,727 B2 | 6/2006 | Phillips et al. |
| 7,172,630 B2 | 2/2007 | Christensen |
| 7,178,218 B1 | 2/2007 | Houser et al. |
| 7,341,603 B2 | 3/2008 | Christensen |
| 7,419,509 B2 | 9/2008 | Christensen |
| 7,462,201 B2 | 12/2008 | Christensen |
| 7,520,904 B2 | 4/2009 | Christensen |
| 7,572,299 B2 | 8/2009 | Christensen |
| 7,578,852 B2 | 8/2009 | Townsend et al. |
| 7,618,464 B2 | 11/2009 | Christensen |
| 7,655,050 B2 | 2/2010 | Palmer |
| 7,686,848 B2 | 3/2010 | Christensen |
| 7,727,285 B2 | 6/2010 | Christensen |
| 7,740,602 B2 | 6/2010 | Christensen |
| 7,771,488 B2 | 8/2010 | Asgeirsson et al. |
| 7,794,506 B2 | 9/2010 | Christensen |
| 7,824,446 B2 | 11/2010 | Christensen et al. |
| 7,846,213 B2 | 12/2010 | Lecomte et al. |
| 7,951,101 B2 | 5/2011 | Pusch |
| 7,955,399 B2 | 6/2011 | Townsend et al. |
| 8,007,544 B2 | 8/2011 | Jonsson et al. |
| 8,034,121 B2 | 10/2011 | Christensen |
| 8,070,828 B2 | 12/2011 | Shannon |
| 8,092,550 B2 | 1/2012 | McCarvill et al. |
| 8,202,325 B2 | 6/2012 | Albrecht-Laatsch et al. |
| 8,246,695 B2 | 8/2012 | Mosler |
| 8,317,877 B2 | 11/2012 | Doddroe et al. |
| 8,474,329 B2 | 7/2013 | Schulze et al. |
| 8,500,825 B2 | 8/2013 | Christensen et al. |
| 8,771,370 B2 | 7/2014 | Albrecht-Laatsch et al. |
| 8,771,372 B1 | 7/2014 | Rubie |
| 8,900,326 B2 | 12/2014 | Doddroe et al. |
| 8,945,238 B2 | 2/2015 | Mosler et al. |
| 9,072,617 B2 | 7/2015 | Halldorsson et al. |
| 9,161,846 B2 | 10/2015 | Mosler |
| 9,351,853 B2 | 5/2016 | Doddroe et al. |
| 2002/0013628 A1 | 1/2002 | Harris |
| 2002/0040249 A1 | 4/2002 | Phillips |
| 2002/0133237 A1 | 9/2002 | Christesen |
| 2002/0188355 A1 | 12/2002 | Chen |
| 2003/0109638 A1 | 6/2003 | Briggs et al. |
| 2004/0225375 A1 | 11/2004 | Chen |

(56) References Cited

U.S. PATENT DOCUMENTS

| | | |
|---|---|---|
| 2004/0236435 A1 | 11/2004 | Chen |
| 2005/0033450 A1 | 2/2005 | Christensen |
| 2005/0033451 A1 | 2/2005 | Aigner et al. |
| 2005/0038525 A1 | 2/2005 | Doddroe |
| 2005/0187640 A1 | 8/2005 | Christensen |
| 2005/0203640 A1 | 9/2005 | Christensen |
| 2005/0216098 A1 | 9/2005 | Christensen |
| 2006/0069450 A1 | 3/2006 | McCarvil et al. |
| 2006/0167563 A1 | 7/2006 | Johnson et al. |
| 2006/0212131 A1 | 9/2006 | Curtis |
| 2006/0224246 A1 | 10/2006 | Clausen |
| 2006/0241783 A1 | 10/2006 | Christensen |
| 2007/0100466 A1 | 5/2007 | Allert |
| 2007/0196222 A1* | 8/2007 | Mosier .................. F04B 45/02 417/472 |
| 2008/0033578 A1 | 2/2008 | Christensen |
| 2008/0167730 A1 | 7/2008 | Pusch |
| 2008/0188951 A1 | 8/2008 | Christensen et al. |
| 2008/0228288 A1 | 9/2008 | Nelson et al. |
| 2008/0312752 A1 | 12/2008 | Miller |
| 2009/0036998 A1* | 2/2009 | Finlinson ............... F04B 45/06 623/34 |
| 2009/0076626 A1 | 3/2009 | Ochoa |
| 2009/0105845 A1 | 4/2009 | Curtis |
| 2009/0157197 A1 | 6/2009 | Bonacini |
| 2009/0204229 A1 | 8/2009 | Mosler et al. |
| 2009/0204231 A1 | 8/2009 | Bonacini |
| 2010/0004757 A1 | 1/2010 | Clausen et al. |
| 2010/0042228 A1 | 2/2010 | Doddroe et al. |
| 2010/0139530 A1 | 6/2010 | Ceballos-Godefroy |
| 2011/0009982 A1 | 1/2011 | King et al. |
| 2011/0029097 A1 | 2/2011 | Ochoa |
| 2011/0197682 A1 | 8/2011 | Palmer |
| 2011/0199101 A1 | 8/2011 | Steele |
| 2011/0202144 A1 | 8/2011 | Palmer |
| 2011/0208322 A1 | 8/2011 | Rifkin et al. |
| 2011/0320012 A1 | 12/2011 | Christensen et al. |
| 2012/0046760 A1 | 2/2012 | Nissels et al. |
| 2012/0179274 A1 | 7/2012 | Christensen |
| 2012/0205206 A1 | 8/2012 | Chen et al. |
| 2012/0209406 A1 | 8/2012 | Chen et al. |
| 2012/0271434 A1 | 10/2012 | Friesen et al. |
| 2013/0030549 A1 | 1/2013 | Zahedi |
| 2013/0066439 A1 | 3/2013 | Zamora et al. |
| 2013/0173023 A1 | 7/2013 | Lecomte et al. |
| 2013/0289742 A1 | 10/2013 | Halldorsson et al. |
| 2014/0018938 A1 | 1/2014 | Bertels et al. |
| 2014/0046456 A1 | 2/2014 | Smith |
| 2014/0156027 A1 | 6/2014 | Smith et al. |
| 2014/0243997 A1 | 8/2014 | Clausen et al. |
| 2014/0336782 A1 | 11/2014 | Mosler et al. |
| 2015/0134081 A1 | 5/2015 | Geiger et al. |
| 2015/0282953 A1 | 10/2015 | Smith et al. |
| 2015/0289996 A1 | 10/2015 | Smith |
| 2016/0000585 A1* | 1/2016 | Sandahl .................. A61F 2/80 623/34 |
| 2016/0038311 A1 | 2/2016 | Gonzalez et al. |
| 2016/0158030 A1 | 6/2016 | Doddroe et al. |

FOREIGN PATENT DOCUMENTS

| | | |
|---|---|---|
| CN | 2075074 U | 9/1990 |
| CN | 2178511 U | 12/1993 |
| CN | 2614649 Y | 5/2004 |
| CN | 2614650 Y | 5/2004 |
| CN | 2614651 Y | 5/2004 |
| CN | 201524155 U | 7/2010 |
| CN | 101621973 A | 12/2011 |
| CN | 200780050083 | 12/2011 |
| CN | 102665614 A | 3/2016 |
| DE | 20307200 U1 | 6/2003 |
| DE | 20307948 U1 | 7/2003 |
| DE | 20307949 U1 | 7/2003 |
| DE | 102014006571 B3 | 8/2015 |
| DE | 102014006687 A1 | 11/2015 |
| EP | 0401864 B1 | 11/1992 |
| EP | 1395209 B1 | 6/2010 |
| TW | 229414 | 11/1993 |
| TW | 339646 | 9/1998 |
| TW | 340371 | 9/1998 |
| TW | 353939 | 3/1999 |
| TW | 382260 | 2/2000 |
| TW | M253331 | 12/2004 |
| TW | M291283 | 6/2006 |
| TW | M336777 U | 7/2008 |
| TW | D124156 | 8/2008 |
| TW | D124157 | 8/2008 |
| TW | M377969 U | 4/2010 |
| TW | M409061 U | 8/2011 |
| TW | M438897 U | 10/2012 |
| TW | M438898 U | 10/2012 |
| TW | M450362 U | 4/2013 |
| TW | M467446 U | 12/2013 |
| TW | M484416 U | 8/2014 |
| WO | 93/24080 A1 | 12/1993 |
| WO | 2005027802 A1 | 3/2005 |
| WO | 2006099580 A2 | 9/2006 |
| WO | 2008070177 A1 | 6/2008 |
| WO | 2011133717 A1 | 10/2011 |
| WO | 2012005856 A1 | 1/2012 |
| WO | 2012009319 A2 | 1/2012 |
| WO | 2013101848 A1 | 7/2013 |
| WO | 2014008306 A1 | 1/2014 |
| WO | 2014147070 A1 | 9/2014 |
| WO | 2015169443 A1 | 11/2015 |

OTHER PUBLICATIONS

Moloney et al., "Parameters determining the strength and toughness of particulate filled epoxide resins," Journal of Materials Science, Feb. 1, 1987, pp. 381-393.

* cited by examiner

SECTION A-A

VACUUM SYSTEM FOR A PROSTHETIC FOOT

CROSS-REFERENCES TO RELATED APPLICATIONS

The present application is a continuation in part of U.S. patent application Ser. No. 16/111,569, filed Aug. 24, 2018, which claims the benefit of U.S. Provisional Application Ser. No. 62/550,107, filed Aug. 25, 2017 and U.S. Provisional Application Ser. No. 62/589,025, filed Nov. 21, 2017; and is a continuation in part of U.S. patent application Ser. No. 16/111,569, filed Aug. 24, 2018, which is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012; and this application is a continuation in part of U.S. patent application Ser. No. 16/111,569, filed Aug. 24, 2018, which is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation in part of U.S. patent application Ser. No. 16/111,569, filed Aug. 24, 2018, which is a continuation in part of U.S. patent application Ser. No. 14/731,818, filed Jun. 5, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation in part of U.S. patent application Ser. No. 16/111,569, filed Aug. 4, 2018, which is a continuation-in-part of U.S. patent application Ser. No. 14/731,771, filed Jun. 5, 2015, which is a continuation of U.S. patent application Ser. No. 13/642,501, filed on Nov. 27, 2012, now U.S. Pat. No. 9,078,773, which is a 371 national phase application of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173 and incorporates the disclosure of all such applications by reference, and this application incorporates the disclosure of all such applications by reference.

BACKGROUND

Prosthetic feet are well known in the art. In use, such prosthetic feet are typically mounted to either an above knee amputation socket or a below knee amputation socket and are designed to mimic the natural gait of a user. Traditionally, the sockets of most amputation types are retained on the user through friction. This friction has been achieved by using socks or liners of various specialized materials. The major drawback with this system has been that over the course of a day, the amputated limb will change its volume, and the friction force will change accordingly. Replacing the friction retention system with a vacuum retention system has proven to be advantageous to the user for many reasons. The biggest reason being that vacuum helps the limb volume to remain more stable which improves socket retention and limb health. Additionally, vacuum systems for prosthetic feet may be provided to further enhance the feel, fit, and function of the foot to the user for all types of lower limb amputation (e.g. above knee, below knee, etc.). Problems exist with vacuum systems including the noise of the electric motor and vacuum pump being disturbing to the user and those nearby and high maintenance requirements due to the complexity of the vacuum system.

SUMMARY

An exemplary vacuum system for a prosthetic foot may comprise a compressible member, a chamber located within the compressible member, and a valve system that connects to the prosthetic socket of the user. The valve system may comprise a valve housing, a pair of valves, an exhaust port, a fitting, an air passageway, and an air return.

Furthermore, the prosthetic foot may comprise a resilient bottom member having a first bottom end and a second bottom end, a resilient top member having a first top end and a second top end, wherein the first top end is connected to the first bottom end of the resilient bottom member, and wherein the resilient top member is connected to a mounting bracket and positioned over the resilient bottom member and directed towards the back of the prosthetic foot.

BRIEF DESCRIPTION OF THE DRAWINGS

A more complete understanding of the present invention may be derived by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

Figure 1:
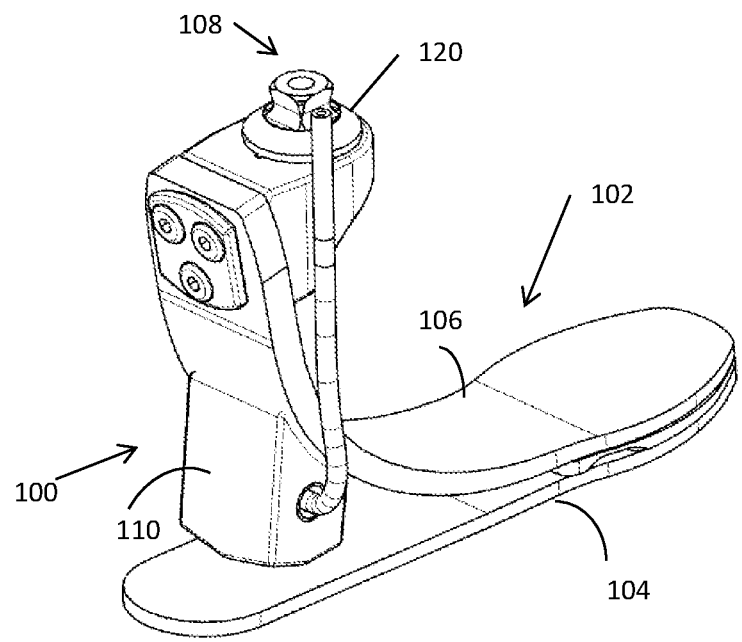
Figure 2:
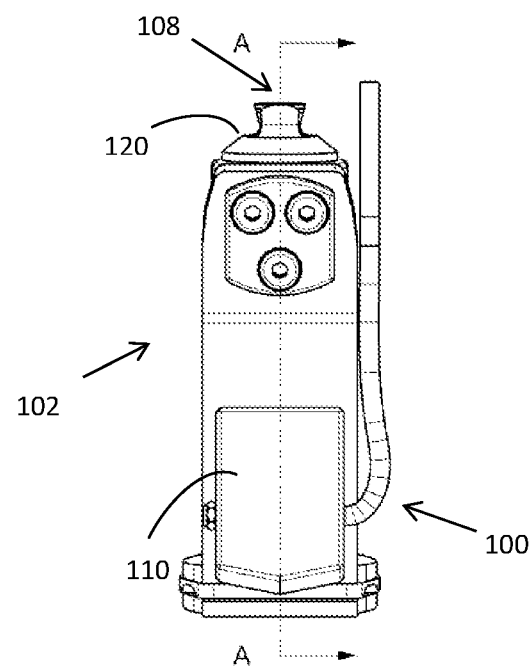
Figure 3:
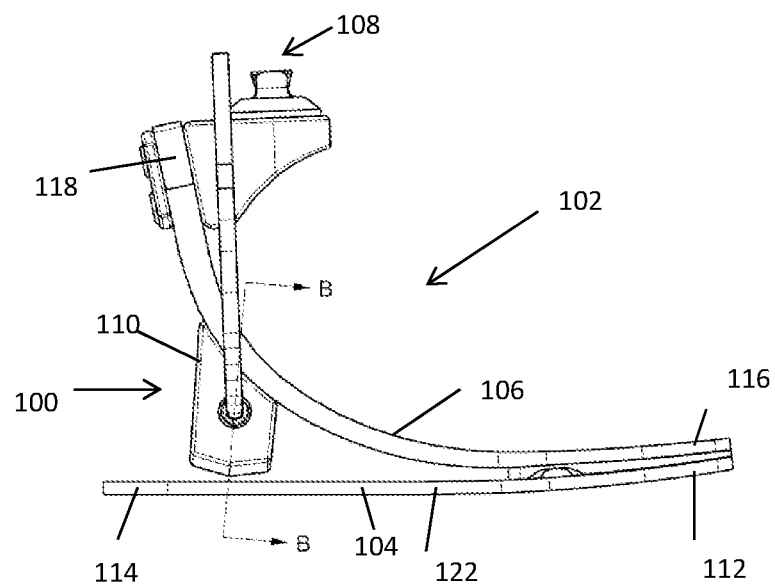
Figure 4:
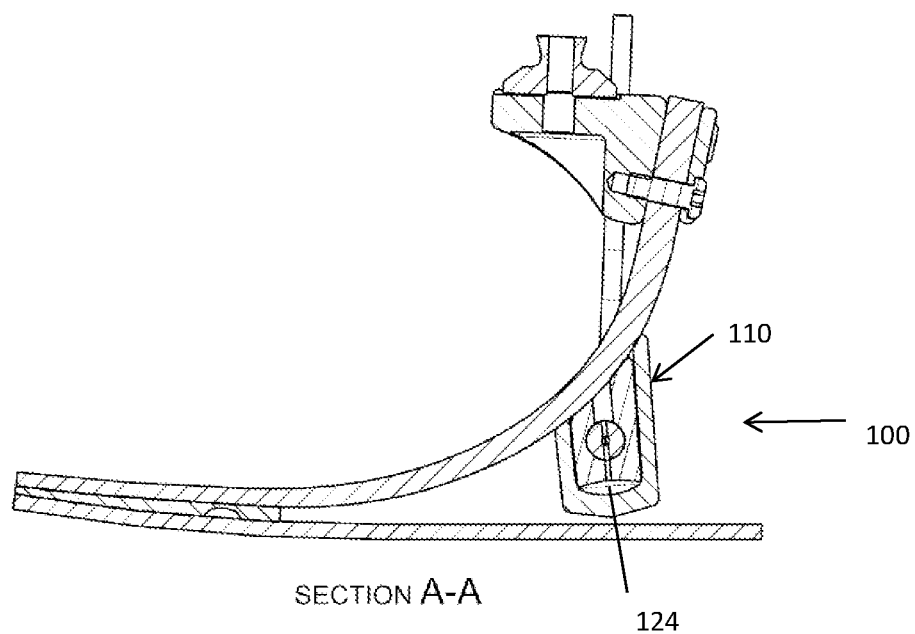
Figure 5:
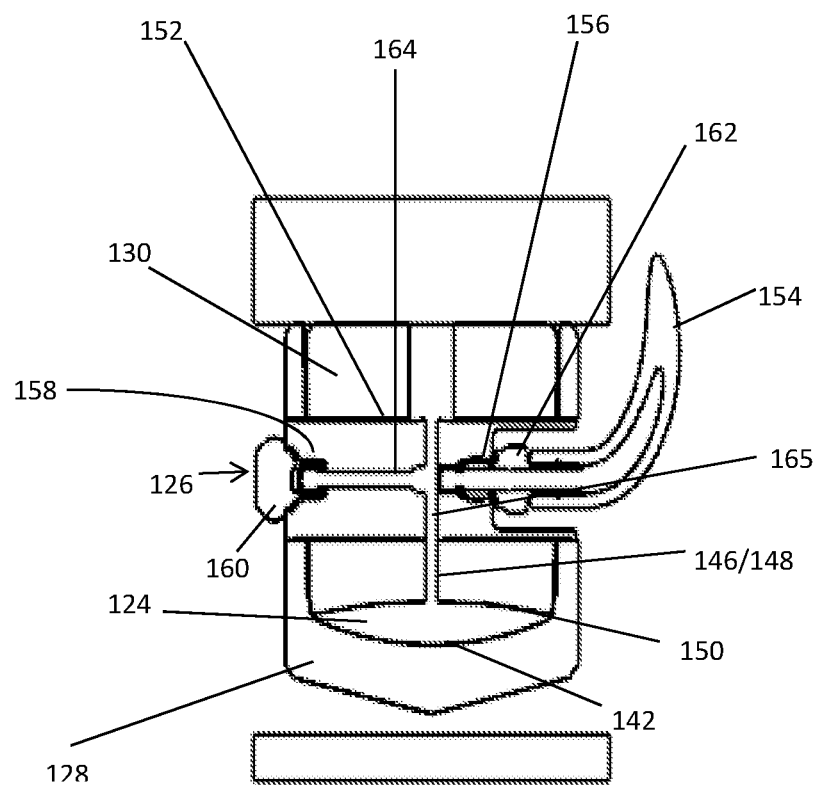
Figure 6:
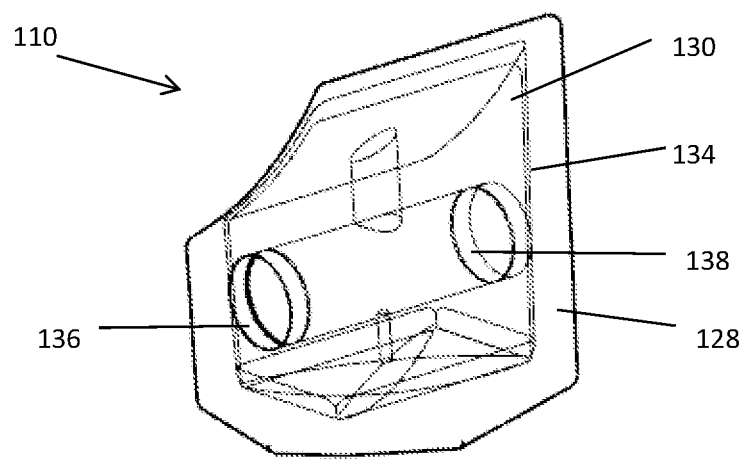
Figure 7:
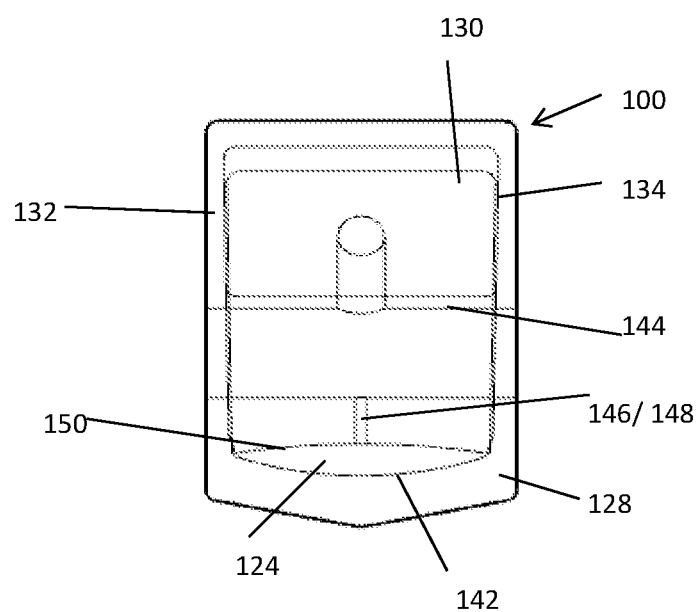
Figure 8:
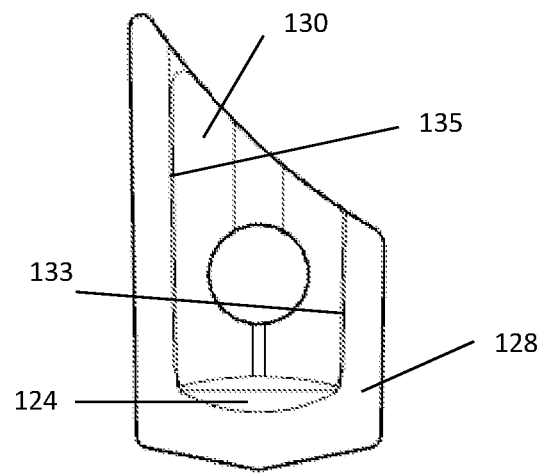
Figure 9:
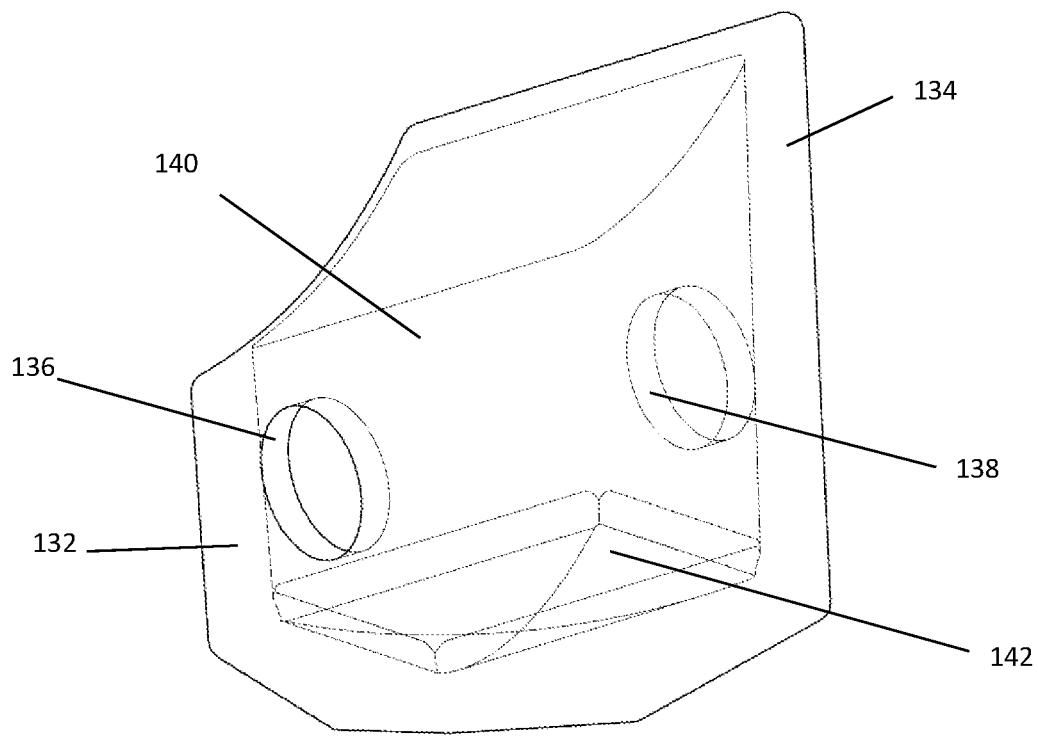
Figure 10:
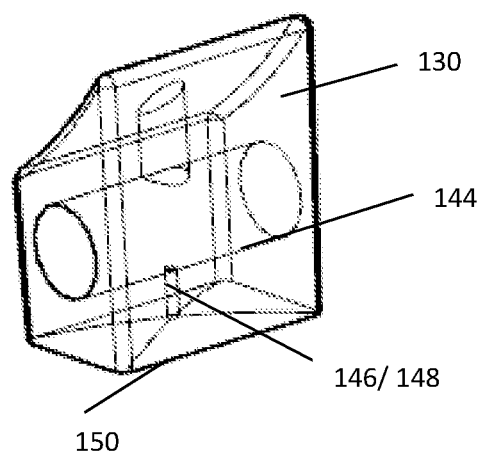
Figure 11:
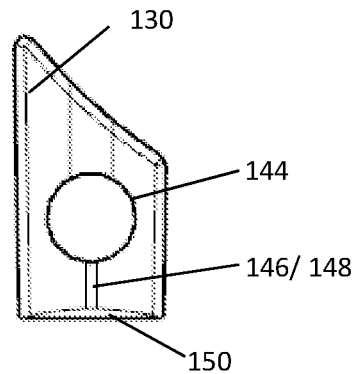
Figure 12:
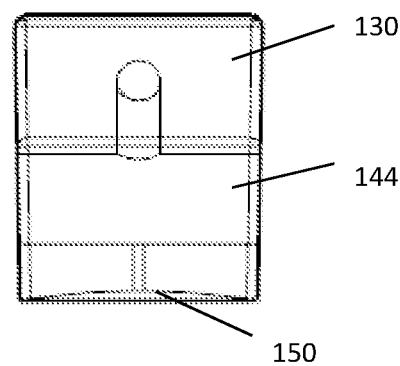
Figure 13:
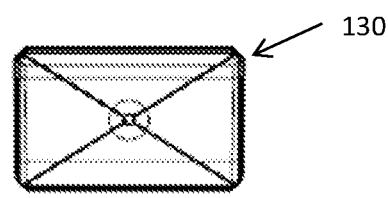
Figure 14A:
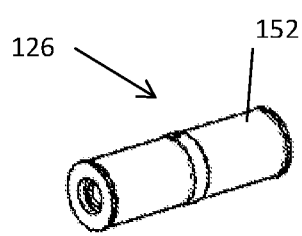
Figure 14B:
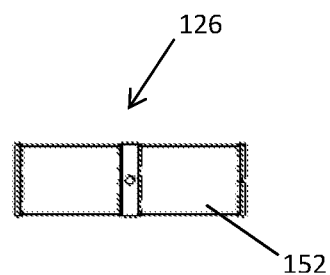
Figure 14C:
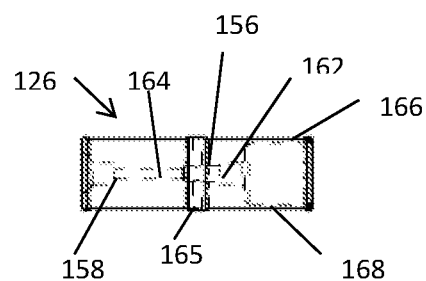
Figure 14D:
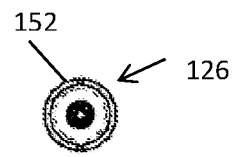
Figure 15:
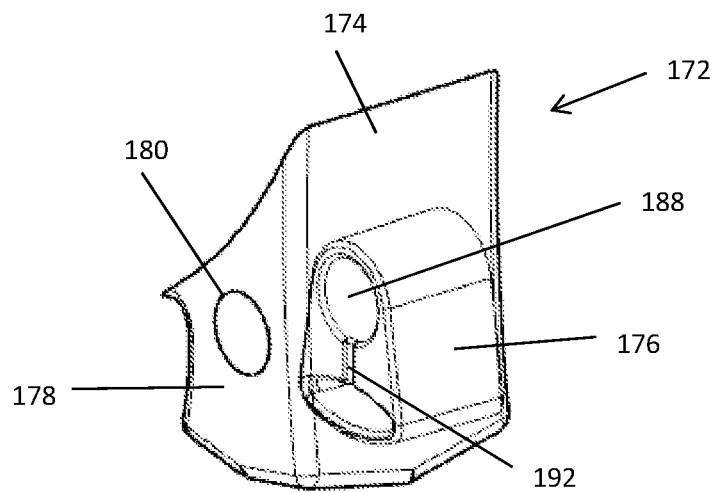
Figure 16:
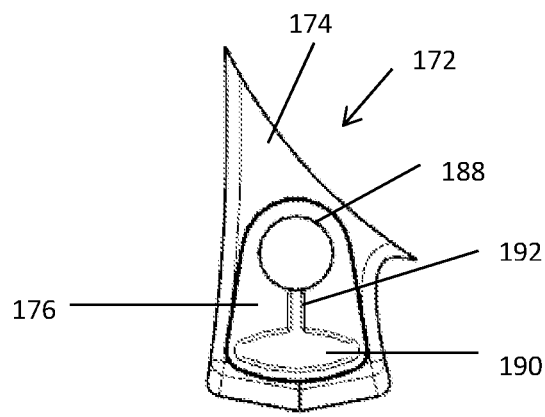
Figure 17:
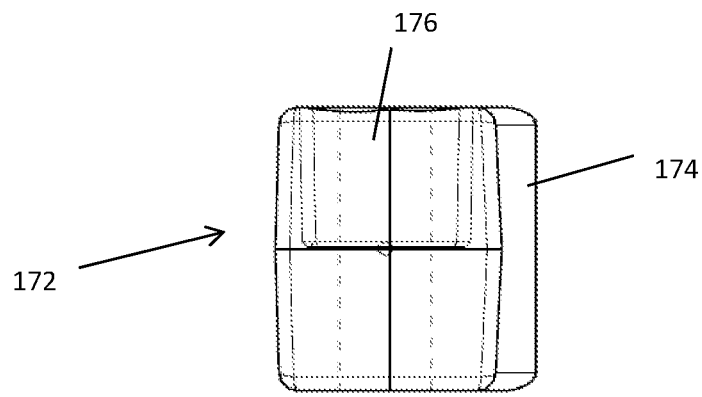
Figure 18:
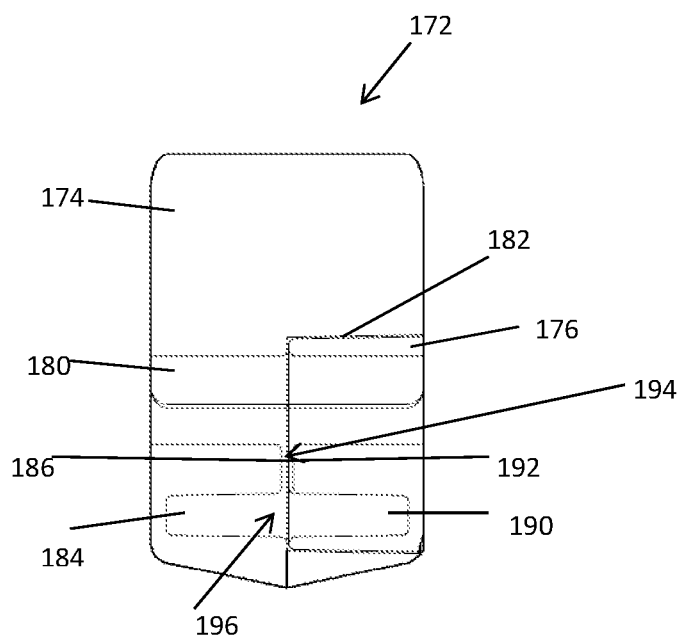
Figure 19:
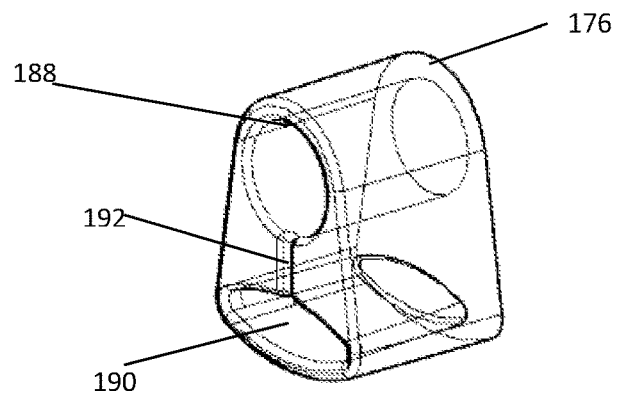
Figure 20:
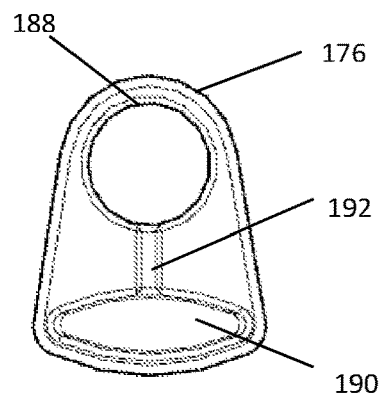
Figure 21:
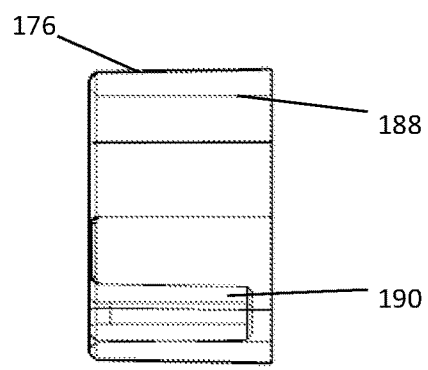
Figure 22:
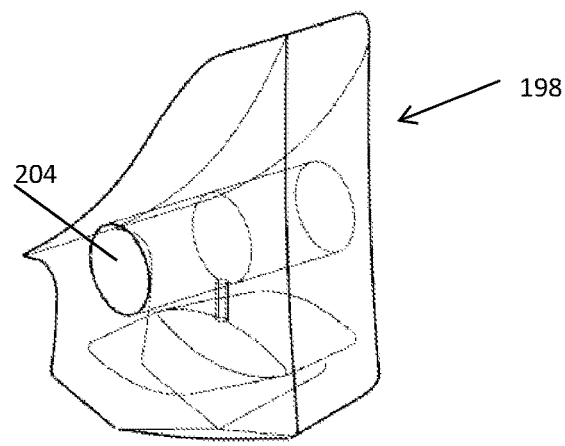
Figure 23:
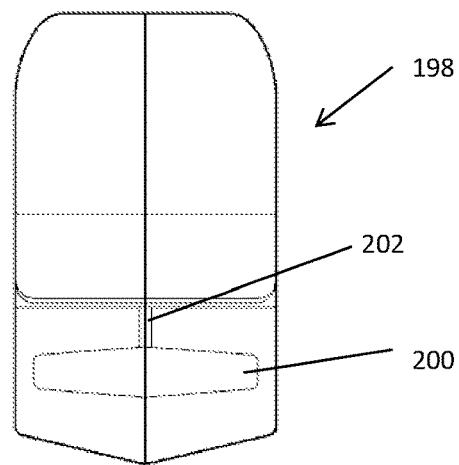
Figure 24:
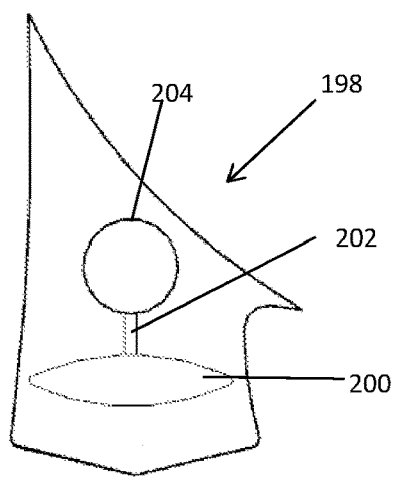
Figure 25:
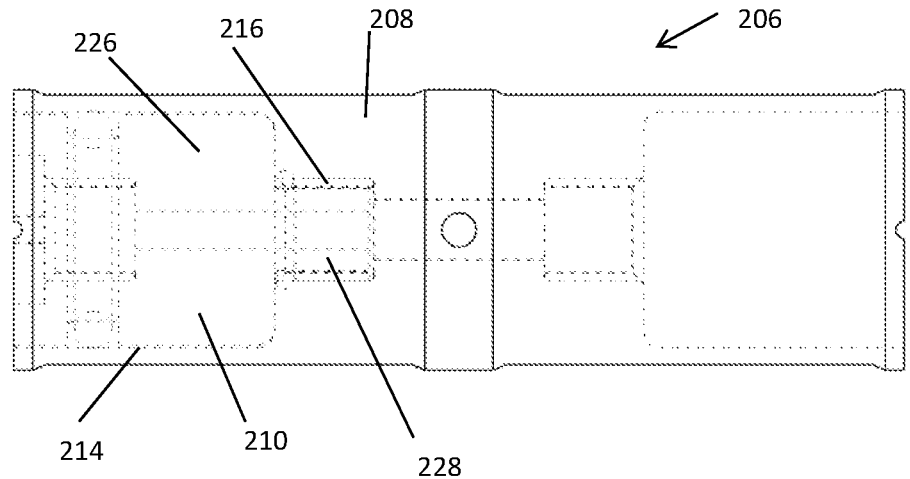
Figure 26:
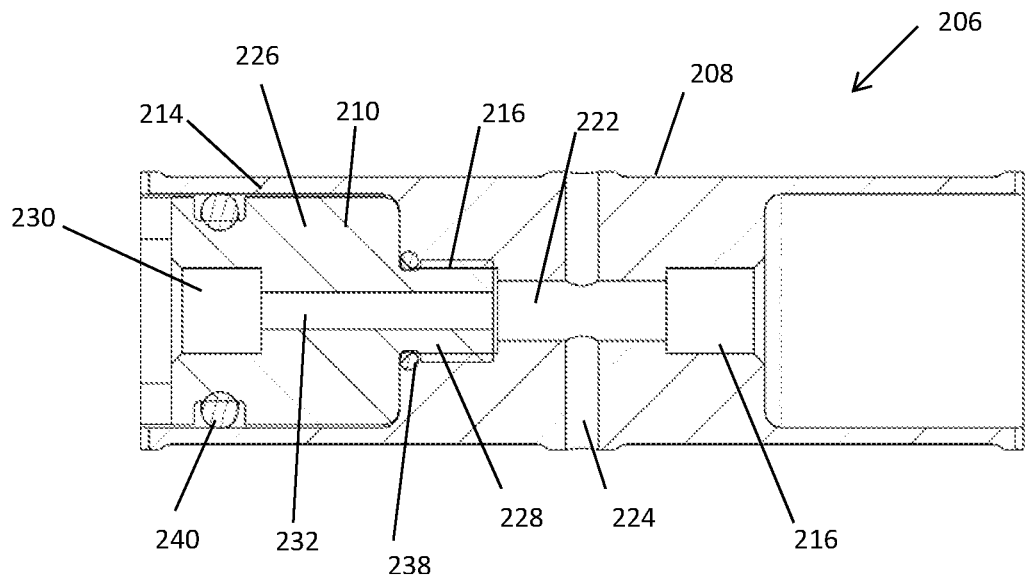
Figure 27:
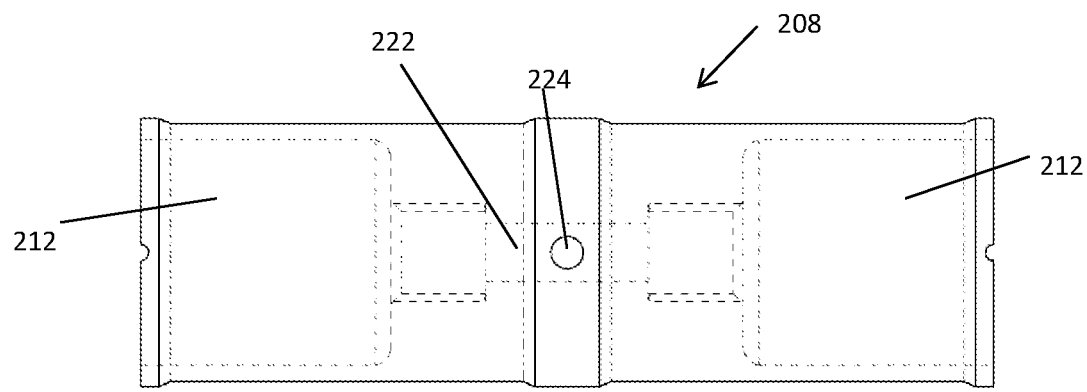
Figure 28:
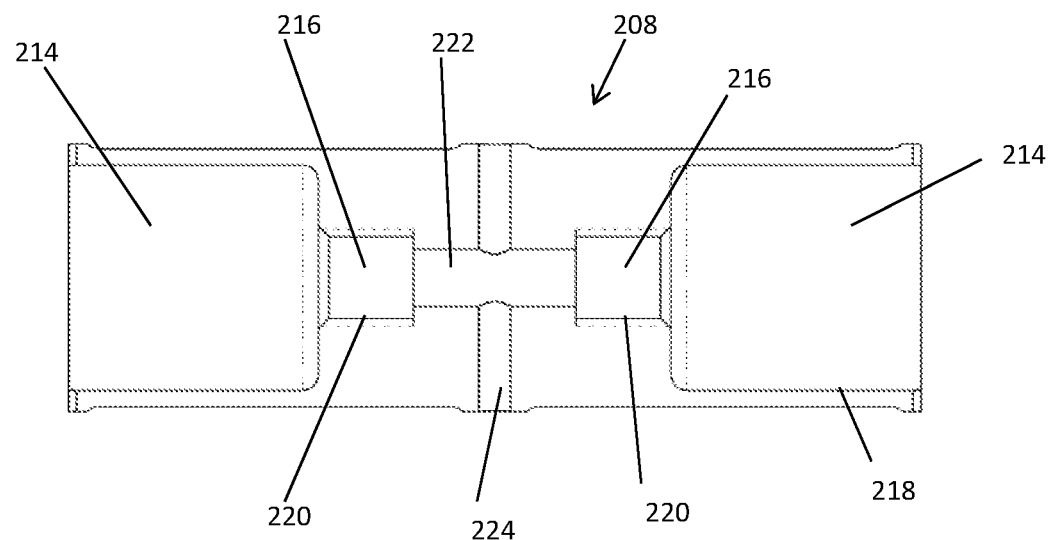
Figure 29A:
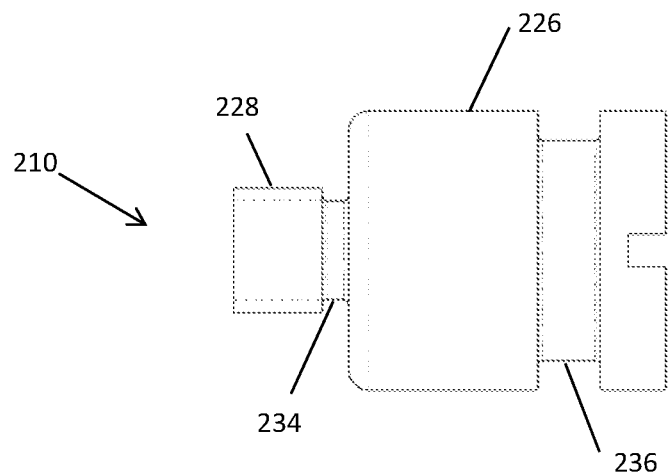
Figure 29B:
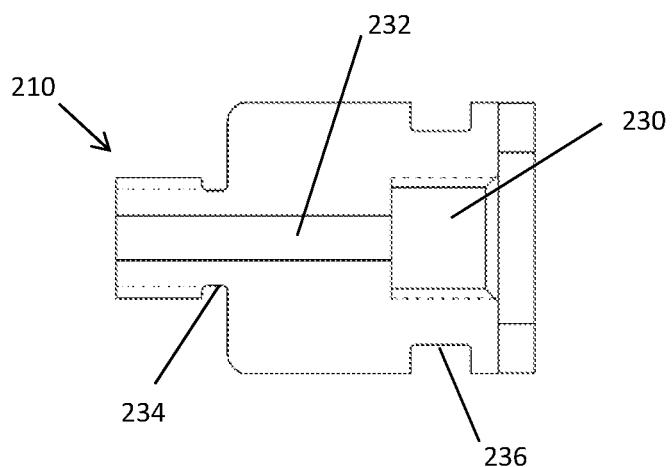
Figure 30:
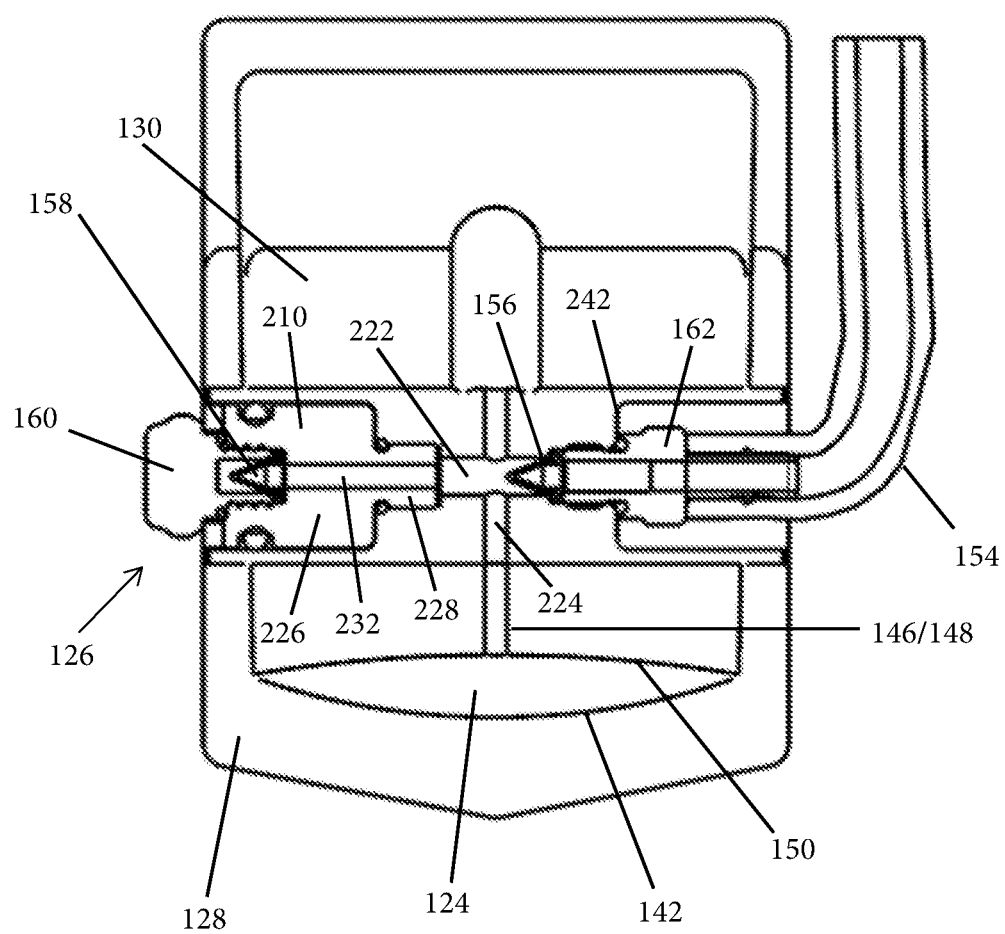

The figures described are for illustration purposes only and are not intended to limit the scope of the present disclosure in any way. Various aspects of the present invention may be more fully understood from the detailed description and the accompanying drawing figures, wherein:

FIG. 1 is a perspective view representatively illustrating a vacuum system on a prosthetic foot in accordance with exemplary embodiments of the present technology;

FIG. 2 is a rear view representatively illustrating the vacuum system on a prosthetic foot in accordance with exemplary embodiments of the present technology;

FIG. 3 is a side view representatively illustrating the vacuum system on a prosthetic foot in accordance with exemplary embodiments of the present technology;

FIG. 4 is a side, cross section view along the line A-A of FIG. 3 representatively illustrating the vacuum system on a prosthetic foot in accordance with exemplary embodiments of the present technology;

FIG. 5 is a partial rear, cross section view along the line B-B of FIG. 3 representatively illustrating the vacuum system on a prosthetic foot in accordance with exemplary embodiments of the present technology;

FIG. 6 is a perspective view of a compressible member with a heel member and a top insert in accordance with exemplary embodiments of the present technology;

FIG. 7 is a rear view of the compressible member with the heel member and the top insert in accordance with exemplary embodiments of the present technology;

FIG. 8 is a side view of the compressible member with the heel member and the top insert in accordance with exemplary embodiments of the present technology;

FIG. 9 is a perspective view of the heel member of the compressible member in accordance with exemplary embodiments of the present technology;

FIG. 10 is a perspective view of the top insert of the compressible member in accordance with exemplary embodiments of the present technology;

FIG. 11 is a side view of the top insert of the compressible member in accordance with exemplary embodiments of the present technology;

FIG. 12 is a rear view of the top insert of the compressible member in accordance with exemplary embodiments of the present technology;

FIG. 13 is a bottom view of the top insert of the compressible member in accordance with exemplary embodiments of the present technology;

FIGS. 14A-D show various views of a valve housing in accordance with exemplary embodiments of the present technology;

FIG. 15 is a perspective view of an additional embodiment of a compressible member with a heel member and a side insert in accordance with exemplary embodiments of the present technology;

FIG. 16 is a side view of the additional embodiment of the compressible member with the heel member with the side insert removed in accordance with exemplary embodiments of the present technology;

FIG. 17 is a bottom view of the additional embodiment of the compressible member with the heel member and the side insert in accordance with exemplary embodiments of the present technology;

FIG. 18 is a rear view of the additional embodiment of the compressible member with the heel member and the side insert in accordance with exemplary embodiments of the present technology;

FIG. 19 is a perspective view of the side insert of the compressible member in accordance with exemplary embodiments of the present technology;

FIG. 20 is a side view of the side insert of the compressible member in accordance with exemplary embodiments of the present technology;

FIG. 21 is a rear view of the side insert of the compressible member in accordance with exemplary embodiments of the present technology;

FIG. 22 is a perspective view of an additional embodiment of a compressible member in accordance with exemplary embodiments of the present technology;

FIG. 23 is a rear view of the additional embodiment of the compressible member in accordance with exemplary embodiments of the present technology;

FIG. 24 is a side view of the additional embodiment of the compressible member in accordance with exemplary embodiments of the present technology;

FIG. 25 shows a top view of the additional embodiment of a valve housing having a valve body and a valve body adaptor with the valve body adaptor installed on the left hand side, with hidden lines to show the internal configuration of the valve housing and the valve body adaptor in accordance with exemplary embodiments of the present technology;

FIG. 26 shows a cross-section, side view of the additional embodiment of the valve housing shown in FIG. 25 with the valve body adaptor installed on the left hand side in accordance with exemplary embodiments of the present technology FIG. 27 shows a top view of an additional embodiment of the valve body with hidden lines to show the internal configuration of the valve body in accordance with exemplary embodiments of the present technology;

FIG. 28 shows a cross-section, side view of the additional embodiment of the valve body shown in FIG. 27 in accordance with exemplary embodiments of the present technology;

FIG. 29A shows a top view of the valve body adaptor in accordance with exemplary embodiments of the present technology;

FIG. 29B shows a cross-section top view of the valve body adaptor shown in FIG. 29A in accordance with exemplary embodiments of the present technology; and FIG. 30 is a partial rear, cross section view along the line B-B of FIG. 3 representatively illustrating the vacuum system on a prosthetic foot with the new embodiment of the valve housing and valve body adaptor along with other components of the valve system but without the upper and lower members of the prosthetic foot in accordance with exemplary embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may be used with a prosthetic foot for various amputation types (above knee, below knee, etc.) In addition, the present technology may be practiced in conjunction with any number of materials and methods of manufacture and the system described is merely one exemplary application for the technology.

While exemplary embodiments are described herein in sufficient detail to enable those skilled in the art to practice the invention, it should be understood that other embodiments may be realized and that logical structural, material, and mechanical changes may be made without departing from the spirit and scope of the invention. This disclosure, its aspects and implementations, are not limited to the specific components or assembly procedures disclosed herein. Many additional components and assembly procedures known in the art consistent with the intended apparatus will become apparent for use with implementations of vacuum systems for prosthetic feet. Thus, the following descriptions are not intended as a limitation on the use or applicability of the invention, but instead, are provided merely to enable a full and complete description of exemplary embodiments.

Briefly, in accordance with exemplary embodiments, a vacuum system for a prosthetic foot is illustrated, which allows for a more comfortable fit of the residual limb to the prosthetic socket of a user. Additionally, studies have shown that elevated vacuum above a certain level is beneficial for residual limb health and maintaining residual limb volume.

A typical prosthetic foot stores energy during the gait cycle and transfers the return potential energy in order to "put a spring in your step." The roll through of a prosthetic foot is defined in the gait cycle as the process from the heel-strike phase to the mid-stance phase to the toe-off phase. The heel-strike phase begins when the heel, or rear portion of the foot touches the ground, and includes the loading response on the foot. The mid-stance phase is when the foot is flat on the ground and the body's center of gravity is over the foot. The toe-off phase is the finish of the stance phase and ends when the tip of the foot is the only portion in contact with the ground, and the load is entirely on the toe/tip of the foot. This is just prior to the swing phase, which constitutes the other half of the gait cycle.

As the user moves through the stance phase portion of the gait cycle the tibia portion of the leg, or that section of the leg defined below the knee, rotates through in relation to the ground. If the mid-stance phase is defined as the lower leg at 90 degrees to the ground, then looking at the side view of an individual, the angle of the lower leg at the heel-strike phase may occur at approximately 65 degrees and the angle of the lower leg at the toe-off phase may occur at approximately 110 degrees. The rotation of the lower leg on the theoretical ankle is notated as tibial progression or lower leg progression during the stance phase. It is through the loads imparted by a user to a prosthetic foot through the stance phase of the gait cycle that a vacuum system may be powered to provide a better fit and feel for the connection of the residual limb of the user and the prosthetic socket throughout the gait cycle.

In accordance with various embodiments and with reference to FIGS. 1-7, a vacuum system 100 for a prosthetic foot 102 is shown. The prosthetic foot 102 may comprise a resilient bottom member 104, a resilient top member 106, a connection point 108 attached to the top member 106 and configured for attachment to a user, and a compressible member 110. The resilient bottom member 104 may have a front end 112 and a rear end 114. The resilient top member 106 may have a front end 116 and a rear top end 118. Further, the front end 112 of the resilient top member 106 can be connected to the front end 116 of the resilient bottom member 104, while the resilient top member 106 can be positioned over the resilient bottom member 104 and directed towards the rear of the prosthetic foot 102.

The connection point 108 may be coupled to the rear top end 118 of the resilient top member and comprise a mounting portion 120. The mounting portion 120 may comprise a spherical dome and an attachment portion, which is a standard male pyramid adapter used in the prosthetic industry. The pyramid adapter may be coupled with a standard receiver used in the practice of prosthetics, for example, a Staats style attachment, which is commonly known in the prosthetic industry. The mounting portion 120 may use a standard receiver adapter, as understood by one of ordinary skill in the art. According to various embodiments the mounting portion 120 may facilitate attachment to the residual limb of the user. The mounting portion 120 may comprise a centerline that is aligned with the weight line of the user.

Moreover and with renewed reference to FIG. 1, the top member 106, bottom member 104, and compressible member 110 transfer energy between themselves in a natural, true foot manner. The loading response during the heel strike phase compresses compressible member 110 and top member 106, which in turn passes energy into, and causes a deflection of, a rear portion of bottom member 104. Energy is transferred towards the front of prosthetic foot 100 during the mid-stance phase. Furthermore, an upward deflection of at least one of bottom member 104 and top member 106 stores energy during the transition from the mid-stance phase to the toe-off phase of the gait cycle.

With respect to the walking motion, the prosthetic foot 102 is configured to increase the surface-to-foot contact through the gait cycle. The increased surface contact allows for a smoother gait cycle, and increases stability in comparison to the typical prior art prosthetics. In exemplary embodiments, the underside of bottom member 104 has different contours that provide increased surface contact for different types of uses.

The resilient bottom member 104 of the prosthetic foot 102 can have various shapes depending on desired use. The desired use may include prosthetic feet for above-knee amputees or prosthetic feet for below-knee amputees. In various embodiments, the prosthetic foot 102 for above-knee amputees may comprise a bottom member 104 having a curved bottom with no inflection point. In one embodiment, the prosthetic foot 102 comprises a resilient bottom member 104 having a partially curved portion from the front end 112 to the rear end 114 of the resilient bottom member 104. In various embodiments, the bottom member 104 may comprise a constant arc due to single radius forming the partial curve of the bottom member 104. In other various embodiments, the curve of the bottom member 104 can be designed as a spline of variable radii. The curve of bottom member 104 in above-knee prosthetic foot facilitates keeping an artificial knee stable because the forces substantially restrict the knee from bending. The curved bottom member 104 enables a rocking motion even if the artificial knee is hyper-extended.

Similarly, the prosthetic foot 102 for below-knee amputees may comprises a bottom member 104 having a partially curved front portion and a substantially linear rear portion. In one embodiment, the prosthetic foot 102 comprises a resilient bottom member 104 having a partially curved portion from the front end 112 to a middle portion 122 and a substantially linear portion from the middle portion 122 to the rear end 114 of the resilient bottom member 104. The front portion from the front end 112 to the middle portion 122 of resilient bottom member 104 may have a constant arc due to single radius forming the partial curve. In various embodiments, the front portion from the front end 112 to the middle portion 122 of resilient bottom member 104 can have a curve designed as a spline of variable radii. In accordance with various embodiments, the rear portion from the middle portion 122 to the rear end 114 of the resilient bottom member 104 can be substantially straight and tangent to the front portion such that bottom member 104 does not have an inflection point. A straight rear portion and a curved front portion of bottom member 104 facilitates rotation of the tibia progressing the natural rotation of the knee forward and preventing hyper-extension of the knee.

In accordance with an exemplary embodiment, resilient bottom and top members 104, 106 may be made of glass fiber composite. The glass fiber composite may be a glass reinforced unidirectional fiber composite. In one embodiment, the fiber composite material is made of multiple layers of unidirectional fibers and resin to produce a strong and flexible material. The fibers may be glass fibers or carbon fibers. Specifically, layers of fiber are impregnated with the resin, and a glass reinforcement layer can be positioned between at least two fiber weave layers. Typically, several layers of the unidirectional fibers or tape are layered together to achieve the desired strength and flexibility. Further, in various embodiments the layers of unidirectional fibers or tape can be oriented at various angles.

The vacuum system 100 may be used with any conventional prosthetic leg (consisting of socket, pylon, etc.). The vacuum system 100 may be configured to connect to any commercially available prosthetic socket designed to work with a vacuum attachment apparatus. Specifically, the vacuum system 100 will connect to an elevated vacuum suspension setup and also should also work with any commercially available prosthetic socket designed for passive suction suspension.

In one embodiment, the vacuum system 100 may be utilized with the existing compressible member 110. In another embodiment, the vacuum system may be added to a foot without a compressible member or used in conjunction with an existing compressible member in a prosthetic foot.

Referring to FIGS. 5-8, the vacuum system 100 for a prosthetic foot may comprise a compressible member 110, a chamber 124 located within the compressible member 110, and a valve system 126 that connects to the prosthetic socket of the user (not shown).

The compressible member 110 may comprise a heel member 128 and a top plug insert 130. In various embodiments, the top plug insert 130 and the heel member 128 can be any suitable shape as contemplated by one of ordinary skill in the art. In various embodiments, the top plug insert 130 may be inserted within the heel member 128 to form the chamber. As shown in FIG. 9, the heel member 128 may comprise a pair of sidewalls 132, 134 with internal bores 136, 138, a front wall 133, a rear wall 135, and a cavity 140 that receives the top plug insert 130. The cavity 140 may comprise an internal surface 142 or any other suitable shape.

Referring now to FIGS. 6, 7, and 10, the top plug insert 130 may comprise an internal bore 144 and a void 146 that function as an air passageway 148. The top plug insert 130 may comprise a concave lower surface 150. When the top plug insert 130 is placed within the cavity 140 the internal bores 136, 138 of heel member 128 align with the internal bore 144 of the top plug insert 130 to receive the valve system 126, shown in FIG. 5. Additionally, the concave internal surface 142 of the cavity 140 and the concave lower surface 150 of the top plug insert 130 form the chamber 124. In various embodiments, the chamber 124 may be generally in the shape of an oblate spheroid, a short or flattened octahedron, a rectangular pillow shape, or any other shape that can be collapsed on itself when a vertical force is applied.

The top plug insert 130 is both bonded in place and mechanically locked by the valve system 126 which protrudes through the internal bores 136, 138 of heel member 128 and the internal bore 144 of the top plug insert 130. The top plug insert 130 may be bonded to the heel member 128 using an adhesive appropriate for bonding two elastomeric deformable materials, such as rubber, together. In various embodiments, the top plug insert 130 and the cavity 140 within the heel member 128 can be any suitable shape as contemplated by one of ordinary skill in the art as long as the top plug insert 130 is capable of being inserted within the cavity 140 within the heel member 128 to create the chamber 124.

In various embodiments, the chamber 124 may be located within the compressible member 110 and is connected to the valve system 126 by the air passageway 148. In one embodiment, the chamber 124 may be formed between the internal surface 142 of the heel member 128 and the lower surface 150 of the top plug insert 130. In one embodiment, chamber 124 may comprise a generally rectangular in shape as shown in FIG. 6. When viewed from the rear, as shown in FIGS. 5 and 7, the chamber 124 is roughly elliptical in shape, which allows the chamber to fully collapse when loaded. In another embodiment, the chamber 124 is generally rectangular when viewed from the side and from the back. In another embodiment chamber 124 may comprise an upside-down T shape when viewed from the side. In one embodiment the volume of chamber 124 is approximately 0.1 to 0.25 cubic inches. It should be understood that any volume contemplated may be used as long as the volume is configured to provide enough back pressure to seal the socket to the residual limb.

The chamber 124 may be connected to the valve system 126 by way of air passageway 148. In various embodiments, the air passageway 148 can be a void in the top plug insert 130 or a separate tube located inside the top plug insert 130. The separate tube comprising air passageway 148 may be a small diameter stainless steel tubing, or small diameter carbon fiber tubing, small diameter flexible plastic tubing, and the like. Alternatively, air passageway 148 may connect chamber 124 to the valve system 126 in a way external to compressible member 110.

It should be noted that in an exemplary embodiment, that there is a single air passageway 148 connecting the chamber 124 to the valve system 126. In various embodiments the air passageway 148 may be bi-directional. Furthermore, the chamber 124 contemplated above may exist solely between the internal surface 142 of the heel member 128 and the lower surface 150 of the top plug insert 130 and may be any suitable shape that can compress and/or collapse on itself. Specifically, in one embodiment, there is not any contemplated internal membrane located within the chamber 124 between the internal surface 142 of the heel member 128 and the lower surface 150 of the top plug insert 130.

In various embodiments and referring now to FIGS. 5-7, the valve system 126 may comprise a valve housing 152 and an air return 154. The valve housing 152 may comprise a pair of valves 156, 158, an exhaust port 160, and a fitting 162. An air chamber 164 connects the pair of valves 156, 158 and allows for air to travel therebetween. A valve housing passageway 165 connects the passageway 148 to the air chamber 164. Air may travel into the housing through valve 156 and out through valve 158. The air return 154 connects to the prosthetic socket of the user, which contains the vacuum attachment apparatus. The air return 154 may comprise standard ⅛ inch diameter tubing used to connect vacuum systems to prosthetic sockets.

In various embodiments, the valve housing 152 may be located within the internal bores 136, 138 of the heel member 128 and the internal bore 144 of the top plug insert 130 of the compressible member 110. In one embodiment, the internal bore 144 of the top plug insert 130 is located within the compressible member 110 and between the sidewalls 132, 134, the front wall 133, and the rear wall 135 of the heel member 128 of the compressible member 110. In one embodiment, the internal bore 144 of the top plug insert 130 is located within the compressible member 110 and between the sidewalls 132, 134, the front wall 133, and the rear wall 135 of the heel member 128 of the compressible member 110 and oriented substantially horizontally therewithin. While the shape of the valve housing 152 of the valve system 126 is shown as generally cylindrical, any configuration and shape may be contemplated. The valve housing 152 may comprise the fitting 162 located at a first end and the exhaust port 160 located at a second end opposite the first end. The internal bores 136, 138 of the heel member 128 and the internal bore 144 of the top plug insert 130 and the valve housing 152 are typically designed with generally the same shape and dimensions such that a tight fit of the valve housing 152 within the internal bore(s) exists.

The fitting 162 may be coupled to the air return 154 at the first end, which in turn may be connected to the user's prosthetic socket that contains the vacuum attachment apparatus (not shown). The first valve 156 may be coupled to the second end of the fitting 162 by any suitable manner. In one embodiment, the fitting 162 has a ⅛ inch internal diameter tube fitting at the first end, and 10-32 UNF threaded connection with an O-ring gasket that seals a mating face 166 of the fitting 162 to an internal wall 168 of the valve housing 152 when fully tightened down and installed within the inner bore 130. An example of the fitting 162 is produced by Pneumadyne® and is part number EB-30-250.

The exhaust port 160 may be coupled to the second end of the valve housing 152. The exhaust port 160 may be coupled to the valve housing 152 in any suitable manner. In one embodiment, the exhaust port 160 may comprise a filtered exhaust port through which the air exiting travels to the atmosphere at a first end of the exhaust port. Some examples of the exhaust port are McMaster-Carr® part number 9833K18 or alternatively Industrial Specialties Mfg. part number BV-1032M-40-B. In one embodiment, the McMaster-Carr® part is sealed using Teflon® tape on the threads of the fitting. In one embodiment, the Industrial Specialties Mfg. part has an O-ring gasket that seals the mating face to the housing when fully tightened within the valve housing 152.

In various embodiments, the second valve 158 may be located adjacent an internal end of the exhaust port 160. The first and second valves 156, 158 may comprise one-way duckbill valves. The one-way duckbill valve design has a very low cracking pressure (to allow air in the designed direction of travel) and does not allow air to travel in the reverse direction. In one embodiment, the one-way duckbill valve is produced by Minivalve International, part number DU027.002-154. The second valve 158 allows air to exit the valve housing 152 into the atmosphere, while the first valve 156 permits air to enter valve housing 152, as will be discussed in detail below. The area between the first valve 156 and second valve 158 may comprise an open-air chamber 164 that allows air to flow between the two valves. This open air chamber 164 is connected to air passageway 148 by the valve housing passageway 165 and provides free air flow to the chamber 124 within the compressible member 110.

In various embodiments and referring now to FIGS. 25 and 26, an additional embodiment of a valve housing 206 is shown. The valve housing 206 may be used with the valve assembly 126 and located within the compressible member 110 in the same manner as described above with respect to valve housing 152.

Referring now to FIGS. 25-29, the valve housing 206 may comprise a valve body 208 and a valve adaptor 210. FIG. 27 shows the valve body 208 rotated 90 degrees from the installed position with dashed lines to show the internal configuration. FIG. 28 shows a cross-section of the valve body 208 in the installed position. The valve body 208 is a universal piece that utilizes the valve adaptor 210 such that the components used with the valve housing 206 can be attached to either side or end of the valve housing 206. The valve body 208 comprises a pair of internal chambers 212 that mirror one another. The internal chambers 212 are generally cylindrical although any contemplated shape may be used. Each of the internal chambers 212 comprises a first chamber 214 and a second chamber 216 located inwardly of the first chamber 214. The first chambers 214 are located adjacent to the ends of the valve body 208 and include an internal wall 218. The second chambers 216 are located inwardly of the first chambers 214 and contain an inner wall 220. The second chambers 216 of each side of the valve body 208 are connected by a horizontal passageway 222. A vertical passageway 224 also exists to communicate with the air passageway 146/148 as will be discussed below.

In various embodiments and referring now to FIGS. 29A and 29B, the valve body 208 may be used in conjunction with the valve adaptor 210. The valve adaptor 210 is shaped to fit within either of the internal chambers 212 of the valve body 208. The valve adaptor 210 may comprise an outer fitting 226 and an inner fitting 228. The valve adaptor 210 outer fitting 226 may comprise an inner recess 230 configured to receive the valve 158 and an air passageway 232, which communicates with the horizontal passageway 222 in the valve body. The valve adaptor 210 may comprise first and second grooved recesses 234, 236 which receive inner and outer O-rings 238, 240 to seal the valve adaptor 210 within the valve body 208.

FIGS. 25 and 26 show a valve adaptor 210 installed on the left side of the valve body 208. The inner fitting 228 is received within the second chamber 216 on the left side of the valve body 208 and the outer fitting 226 is received within the first chamber 214 on the left side of the valve body 208. When installed, the valve adaptor 210 utilizes the inner and outer O-rings 238, 240 to seal the valve adaptor 210 within the valve body 208.

In various embodiments, FIG. 30 shows the remainder of the components of the valve system 122 used in conjunction with the valve body 208 and valve adaptor 210. The valve adaptor 210 is shown installed on the left side of the valve body 208. It should be understood that that the valve adaptor 210 may be installed on either side of the valve body 208. Referring to FIGS. 26 and 30, the inner fitting 228 is received within the second chamber 216 of the valve body 208 and the outer fitting 226 is received with the first chamber 214 of the valve body 208.

In various embodiments, the fitting 162 may be received within the second chamber 216 of the valve body 208. The first valve 156 is coupled to the fitting 162 and extends within the horizontal passageway 222. As described above the fitting 162 may be coupled to the air return 154 at the first end, which in turn may be connected to the user's prosthetic socket that contains the vacuum attachment apparatus (not shown). The first valve 156 may be coupled to the second end of the fitting 162 by any suitable manner. In one embodiment, the fitting 162 has a ⅛ inch internal diameter tube fitting at the first end, and 10-32 UNF threaded connection with an O-ring gasket that seals a mating face 166 of the fitting 162 to an internal wall 242 of the valve body 208. An example of the fitting 162 is produced by Pneumadyne® and is part number EB-30-250.

In various embodiments, the second valve 158 may be received within the inner recess 230 of the valve adaptor 210. The exhaust port 160 is received within the second valve 158. The first and second valves 156, 158 may comprise one-way duckbill valves. The one-way duckbill valve design has a very low cracking pressure (to allow air in the designed direction of travel) and does not allow air to travel in the reverse direction. In one embodiment, the one-way duckbill valve is produced by Minivalve International, part number DU027.002-154. The second valve 158 allows air to exit the valve housing 206 into the atmosphere, while the first valve 156 permits air to enter valve housing 206, as will be discussed in detail below. The first valve 156 and second valve 158 are connected by the air passageway 232, which communicates with the horizontal passageway 222 in the valve body and allow air to flow between the two valves. The horizontal passageway 222 is connected to air passageway 148 provides free air flow to the chamber 124 within the compressible member 110.

The valve housing passageway 224 connects the passageway 148 to the horizontal passageway 222. Air may travel into the housing through valve 156 and out through valve 158. The air return 154 connects to the prosthetic socket of the user, which contains the vacuum attachment apparatus. The air return 154 may comprise standard ⅛ inch diameter tubing used to connect vacuum systems to prosthetic sockets.

In operation, when a downward force is applied to the prosthetic foot 102, the compressible member 110 and the chamber 124 located therein are compressed when they come into contact with the resilient bottom member 104. The compression of the chamber 124 within the compressible member 110 forces air out of the chamber 124 up through air passageway 148 and into valve housing 152, 206. The pressurized air exits the valve housing 152, 206 through the second valve 158 and the exhaust port 160. When the downward force on the prosthetic foot 102 is reduced or eliminated, the compressible member 110 returns the chamber 124 back to a maximum volume state due to the elastic properties of compressible member 110. The elastic properties and geometry of compressible member 110 allow chamber 124 to expand back to the initial volume when the downward force is eliminated or reduced to the point that the compressible member 110 is no long in contact with the resilient bottom member 104. The second valve 158 then closes and prevents a backflow of air into the valve housing 152, 206 through the exhaust port 160. This causes a negative pressure in valve housing 152, 206. The negative pressure draws air into the valve housing 152, 206 through first valve 156 by way of the fitting 162 and the air return 154. The air return 154 is connected to a prosthetic socket that is designed for an elevated vacuum suspension and the like. The elevated vacuum suspension socket is a commercially available prosthetic socket that uses an elevated vacuum level inside the socket to secure the socket to the amputee's residual limb.

In various embodiments, the compressible member 110 comprises an elastomeric bumper member having a tapered surface configured to contact the resilient bottom member 104 and attached to an underside of a rear top end of the upper member 106. The compressible member 110 can be vertically oriented with respect to the prosthetic foot 102. The compressible member 110 can act as a heel shock for absorbing force on the downward strike during the user's stride and returns energy during the rest of the gait cycle.

In various embodiments, the compressible member 110 can be made from an elastomeric material. In one embodiment, the elastomeric material may be constructed of natural, synthetic or a hybrid mixture of both natural and synthetic rubber. The elastomeric material has about 80% or greater energy return. In another embodiment, the elastomeric material has about 90% or greater energy return. The compressible member 110 can be designed to behave similar to a non-linear spring, thereby allowing larger deflection of the posterior toe during the heel strike. The progressive "spring rate" may lead to a soft initial heel strike but quickly and gently arrests deflection as the compressible member 110 compresses. One benefit of the compressible member 110 is being relatively lightweight in comparison to a prosthetic foot with coiled springs.

As seen in FIG. 4, the compressible member 110 can be located posterior to a vertical axis of the connection point of the mounting portion 120. This enhances the aforementioned and desirable trait of tibial progression. The compressible member 110 can be attached to the underside of the resilient top member 106 in various manners. For example, the compressible member 110 can be fixedly attached using adhesive or fasteners, such as screws. In another example, the compressible member 110 may be detachable using fasteners for replacement purposes. Moreover, in other embodiments, the compressible member 110 can be attached to various locations on the underside of the resilient top member 106 or topside of the resilient bottom member 104. In various embodiments, the prosthetic foot 100 in a static mode has a gap between the compressible member 110 and the resilient bottom member 104. For example, a gap of about ¹⁄₁₀ inch may be present between the compressible member 110 and the resilient bottom member 104. In other various methods, the compressible member 110 can be in contact with both the resilient top member 106 and the resilient bottom member 104 when the prosthetic foot 100 is in a static position. The lack of a gap results in the compressible member 110 being continuously compressed during the gait cycle, though the compressible member 110 is a compression member and not a tension member since the compressible member 110 is only attached to either the top member 106 or the resilient bottom member 104. It is important to the design of the compressible member such that it is only attached to one or the other of the resilient top member 106 and the resilient bottom member 104 and not to both. Connecting the compressible member 110 to both the resilient top and bottom members 106, 104 creates almost a triangle structure, which is very stiff.

The compressible member 110 can be in many shapes. In various embodiments, the detached portion of the compressible member 110 may have a conical, rectangular, or pyramid shape. The tapered surface of the compressible member 110 can terminate in an apex or hemispherical shape, and the apex can be configured to contact the resilient bottom member 104 in response to deflection of the prosthetic foot 100. Moreover, in various embodiments, the compressible member 110 can terminate in multiple points. The tapered compressible member 110 facilitates a damping of vibration and sound generated during heel strike or release. Furthermore, in various embodiments the extruding portion of the compressible member 110 may be any shape that is non-flat surface. Further, a non-flat surface enhances lateral flexibility if the heel strike is not vertical.

The prosthetic foot 100 can be adjusted to accommodate a user in part by adjusting characteristics of the compressible member 110. For example, in various embodiments, the durometer of the compressible member 110 can be increased for users with more heel strike force, which may be caused by additional weight or dynamic activity. A heavier user may be better-suited using a compressible member 110 with a large cross-sectional area compared to a lighter user using a compressible member 110 with a small cross-sectional area. The adjustable durometer of the elastomeric material used for the compressible member 110 allows the adjustment of spring rate of the elastomeric heel based on user needs such as activity level, compliance level, weight changes, and the like. Increased durometer can also adjust the ability of chamber 124 to return to the initial volume after being compressed.

In various embodiments, and referring now to FIGS. 15-21, an additional embodiment of a compressible member 172 may comprise a heel member 174 and a side plug insert 176. The valve system 126 described above may be implemented with the compressible member 172. The heel member 174 comprises a sidewall 178 with internal bore 180, a cavity 182 that receives the side plug insert 176 and a pair of internal voids 184, 186.

The side plug insert 176 may comprise an internal bore 188 and a pair of voids 190, 192. When the side plug insert 176 is placed within the cavity 182 the internal bore 180 of heel member 174 aligns with the internal bore 188 of the side plug insert 176 to receive the valve system 126 (not shown). Additionally, the pair of internal voids 190, 192 of the side plug insert and the pair of internal voids 184, 186 of the heel member 174 combine to form an air passageway 194 and a chamber 196.

The side plug insert 176 is both bonded in place as discussed above, and mechanically locked by the valve system 126 which protrudes through the internal bore 180 of heel member 174 and the internal bore 188 of the side plug insert 176. It should be understood that orientation of the side plug insert and heel member may be reversed, for example, the side plug insert can be placed in a cavity on either side of the heel member.

Referring now to FIGS. 22-24, the vacuum system 100 for a prosthetic foot may comprise a compressible member 198, a chamber 200 located within the compressible member 198, and the valve system 126 that connects to the prosthetic socket of the user (not shown).

In various embodiments the chamber 200 may be located within the compressible member 198 and is connected to the valve system 126 by an air passageway 202. The valve system 126 described above may be implemented with a bore 204 located within the compressible member 198. In one embodiment, the chamber 200 may be formed by molding in a void in each left and right halves of compressible member 198 and consequently bonding the left and right halves of compressible member 198 into a single piece. In one embodiment, the chamber 200 may be formed by molding in a void and sealing the void at one end with a separate piece made of the same material as the compressible member 198 and bonding it into place. In various embodiments, chamber 200 may be formed by 3D printing the material or by a material removal process, such as, cutting or machining and drilling the material. In one embodiment, chamber 200 may comprise a generally rectangular in shape when viewed from the top. When viewed from the rear and side, as shown in FIGS. 23 and 24, the chamber 200 is roughly elliptical in shape, which allows the chamber 200 to fully collapse when loaded. In another embodiment, chamber 200 is generally rectangular when viewed from the side and from the back. In another embodiment, the chamber 200 may comprise an upside-down T shape when viewed from the side or rear. In one embodiment the volume of chamber 200 is approximately 0.1 to 0.25 cubic inches. It should be understood that any volume contemplated may be used as long as the volume is configured to provide enough back pressure to seal the socket to the residual limb.

The chamber 200 may be connected to valve housing 152, 206 by way of the air passageway 202. In various embodiments, the air passageway 202 can be a void in the heel mold or a separate tube located inside compressible member 198 or located between the left and right halves of the compressible member 198. The separate tube comprising air passageway 202 may be small diameter stainless steel tubing, or small diameter carbon fiber tubing, small diameter flexible plastic tubing, and the like. Alternatively, air passageway 202 may connect chamber 200 to valve housing 152, 206 in a way external to compressible member 198.

It should be understood that the compressible members 172, 198 are shaped, located, oriented, constructed, and attached to the prosthetic foot similarly to the compressible member 110 discussed above. It should be understood that the compressible members 172, 198 also function similarly to the compressible member 110 discussed above.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to a preferred embodiment. However, changes and modifications may be made to the preferred embodiment without departing from the scope of the present technology. These and other changes or modifications are intended to be included within the scope of the present technology, as expressed in the following claims.

The invention claimed is:

1. A prosthetic foot for use with a prosthetic socket containing a vacuum attachment apparatus and configured to attach to a residual limb, the prosthetic foot comprising:
   a resilient bottom member comprising a front end and a rear end;
   a resilient top member comprising a front end and a rear end, wherein the front end of the resilient top member is connected to the front end of the resilient bottom member, and wherein the resilient top member is positioned over the resilient bottom member; and a vacuum system coupled to an underside of the top member, the vacuum comprising:
  a compressible member comprising:
    a heel member comprising a pair of sidewalls, a front wall, a rear wall, and a cavity; and
    a top plug insert that is received between the sidewalls and within the cavity to form a chamber;
  a universal valve system received within the compressible member and configured for either a right footed or left footed user;
  a passageway connecting the universal valve system and the chamber within the compressible member; and
  an air return coupled to the universal valve system and the vacuum attachment apparatus.

2. The prosthetic foot of claim 1, wherein an upper internal surface of the cavity and a lower surface of the top plug insert form the chamber.

3. The prosthetic foot of claim 1, wherein each of the pair of sidewalls of the heel member comprise an internal bore.

4. The prosthetic foot of claim 3, wherein the top plug insert comprises an internal bore.

5. The prosthetic foot of claim 4, wherein when the top plug insert is received within the heel member, the internal bores of the heel member align with the internal bore of the top plug insert to receive the valve system and lock the top plug insert within the heel member.

6. The prosthetic foot of claim 1, wherein the top plug insert is coupled within the heel member.

7. The prosthetic foot of claim 6, wherein the top plug insert is bonded within the heel member.

8. The prosthetic foot of claim 7, wherein the top plug insert is bonded within the heel member using an adhesive.

9. The prosthetic foot of claim 1, wherein the chamber is compressed when the compressible member contacts the resilient bottom member in response to an applied downward force on the resilient top member.

10. The prosthetic foot of claim 9, wherein the compression of the chamber within the compressible member forces air out of the chamber through the passageway and out of the valve system.

11. The prosthetic foot of claim 9, wherein upon removal of the downward force, the chamber expands causing a negative pressure within the valve system and activates the vacuum attachment apparatus through the air return.

12. The prosthetic foot of claim 11, wherein the chamber is configured to expand due to the elastomeric properties of the compressible member.

13. The prosthetic foot of claim 1, wherein the universal valve system comprises:
  a valve body comprising a first internal chamber and a second internal chamber;
  a valve adaptor configured to fit within one of the first internal chamber or the second internal chamber;
  a first valve coupled to the valve adaptor;
  a second valve coupled to the other of the first internal chamber or the second internal chamber opposite the connection of valve adaptor;
  an air chamber located within the valve body between the first internal chamber and the second internal chamber;
  an exhaust port coupled to the second valve; and
  the air return coupled to the first valve.

14. The prosthetic foot of claim 13, wherein the passageway is in air communication with the cavity in the compressible member and the air chamber in the valve body.

15. A prosthetic foot for use with a vacuum attachment apparatus and configured to attach to a residual limb, the prosthetic foot comprising:
  a resilient bottom member comprising a front end and a rear end;
  a resilient top member comprising a front end and a rear end, wherein the front end of the resilient top member is connected to the front end of the resilient bottom member; and
  a vacuum system coupled to an underside of the rear end of the top member, the vacuum system comprising:
    a compressible member, comprising:
      a heel member comprising a pair of sidewalls, a front wall, a rear wall, and a cavity; and
      a top plug insert that is received between the sidewalls and within the cavity to form a chamber;
    a universal valve system received within the compressible member and configured for either a right footed or left footed user;
    a single passageway connecting the universal valve system and the chamber; and
    an air return coupled to the universal valve system and the vacuum attachment apparatus.

16. The prosthetic foot of claim 15, wherein an upper internal surface of the cavity and a lower surface of the top plug insert form the chamber.

17. The prosthetic foot of claim 16, wherein the chamber is compressed when the compressible member contacts the resilient bottom member in response to an applied downward force on the resilient top member.

18. The prosthetic foot of claim 16, wherein upon removal of the downward force, the chamber expands causing a negative pressure within the valve system and activates the vacuum attachment apparatus through the air return.

19. A vacuum system for use with a prosthetic socket containing a vacuum attachment apparatus and a prosthetic foot comprising a resilient bottom member and a resilient top member, wherein an underside of a front end of the resilient top member is coupled to a front end of the resilient bottom member, the vacuum system comprising;
  a compressible member configured to be coupled to the underside of the rear end of the resilient top member, the compressible member comprising:
    a heel member comprising a pair of sidewalls, a front wall, a rear wall, and a cavity; and
    a top plug insert that is received between the sidewalls, the front wall, the rear wall and within the cavity to form a chamber;
  a universal valve system received within the compressible member and configured for either a right footed or left footed user;
  a single passageway connecting the universal valve system and the chamber; and
  an air return configured to couple the universal valve system and the vacuum attachment apparatus,
wherein the chamber is configured to be compressed when the compressible member contacts the resilient bottom member in response to an applied downward force on the resilient top member, and wherein the chamber is configured so as to expand upon removal of the downward force which in turn would cause negative pressure within the valve system and activation of the vacuum attachment apparatus through the air return.

* * * * *